United States Patent [19]

Pilgrim

[11] 4,090,506
[45] May 23, 1978

[54] DIAGNOSTIC INSTRUMENT

[75] Inventor: William S. Pilgrim, Port Byron, N.Y.

[73] Assignee: Welch Allyn, Inc., Skaneateles Falls, N.Y.

[21] Appl. No.: 783,166

[22] Filed: Mar. 31, 1977

[51] Int. Cl.² .............................................. A61B 1/06
[52] U.S. Cl. .......................................... 128/11; 32/69;
362/139; 350/172; 350/288; 350/308; 128/22
[58] Field of Search ........................ 128/10, 11, 21, 22;
240/1 LP, 4.2, 2.18; 350/96 B, 288, 172, 308;
32/69, DIG. 7

[56] References Cited

U.S. PATENT DOCUMENTS

| 687,617 | 11/1901 | Ebi ......................................... 128/11 |
| 793,463 | 2/1931 | Cameron .................................. 128/11 |
| 3,884,222 | 5/1975 | Moore ...................................... 128/11 |

Primary Examiner—Robert W. Michell
Assistant Examiner—Henry S. Layton
Attorney, Agent, or Firm—Bruns & Jenney

[57] ABSTRACT

A device for visually examining a generally inaccessible body cavity, such as the larynx or the like, including a mirror mounted upon an elongated support member for insertion and positioning within the cavity, a light transmitting means having a light receiving face positioned adjacent a source of the illumination outside the cavity and a light exit face positioned adjacent to the mirror within the cavity for focusing a small light beam upon a portion of the mirror. A clear aperture is provided in the mirror that is positioned in reference to the incident light beam to allow a portion of the light to pass through the mirror. The region directly behind the mirror is thus illuminated to permit the mirror to be rapidly and accurately positioned by the examiner.

12 Claims, 4 Drawing Figures

U.S. Patent    May 23, 1978    4,090,506
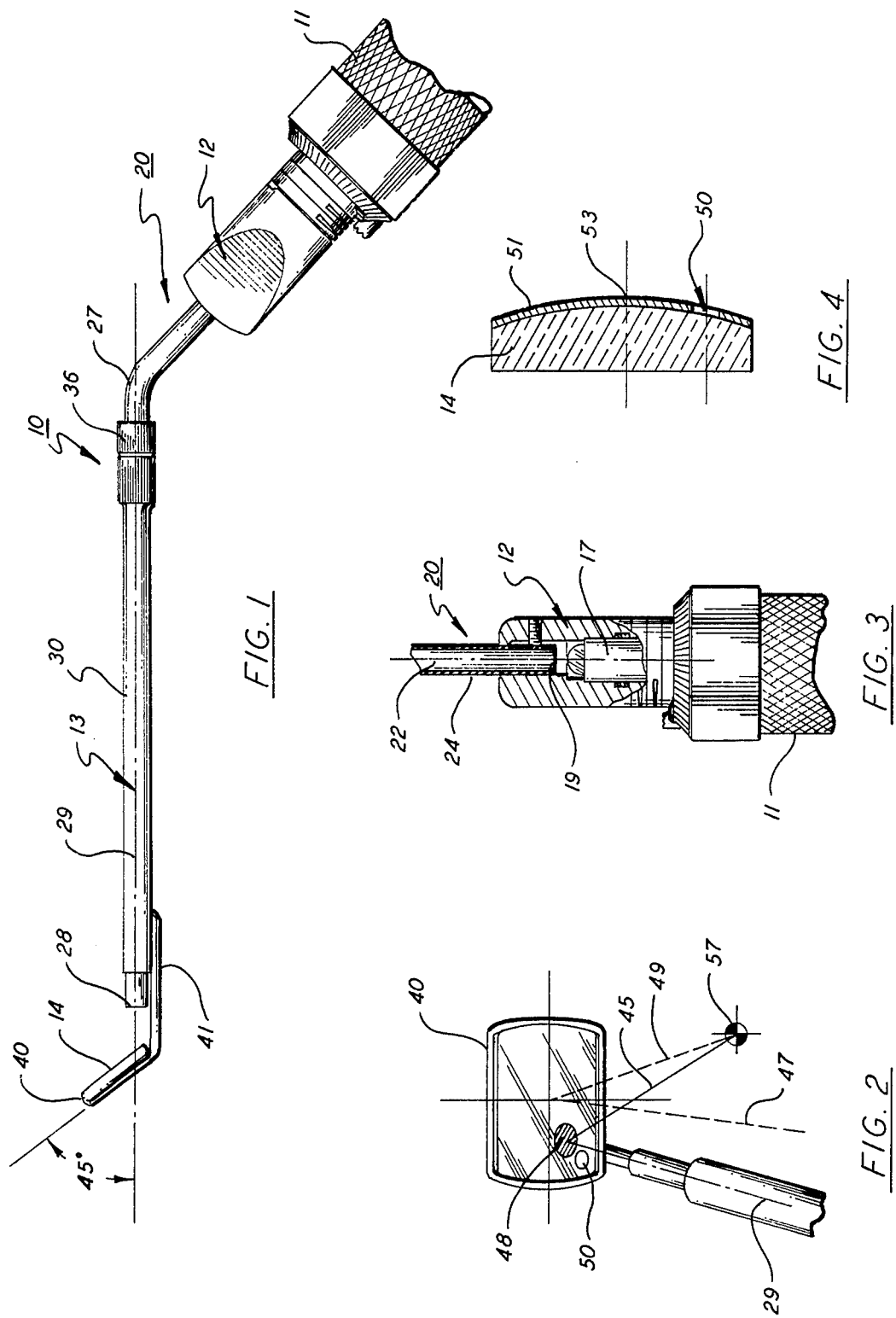

DIAGNOSTIC INSTRUMENT

BACKGROUND OF THE INVENTION

This invention relates to a laryngoscope or the like for examining generally inaccessible cavities and structures such as the larynx, pharynx, naso-pharynx and, in particular, to an optical viewing device for reducing the amount of time consumed in carrying out such an examination.

Most examinations of this nature require insertion and positioning of an optical viewing device into the relatively inaccessible cavity. Because of the relatively small amount of space available and the generally poor lighting conditions prevailing, it has heretofore been difficult to properly position the instrument within the cavity. As a result, what should normally be a relatively short diagnostic examination can oftentimes take an appreciable amount of time.

This problem is particularly critical when examining the larynx or naso-pharynx. If the instrument is allowed to touch the base of the tongue or other sensitive areas, a gag reflex is initiated in the subject which invariably interrupts the examination. This unwanted contact generally occurs simply because there is insufficient lighting available to enable the examiner to properly position the mirror within the cavity. Although some mirror devices are equipped with light sources, as evidenced by the U.S. Pat. No. 3,884,222, the illumination is generally focused by the mirror into the viewing region rather than into the region in which the instrument is physically positioned. As a consequence, this illumination does little in the way of helping the examiner in properly positioning the device and avoiding contact with sensitive areas.

SUMMARY OF THE INVENTION

It is therefore an object of the present invention to improve laryngoscopes and the like.

It is a further object of the present invention to improve optical viewing devices for examining generally inaccessible body cavities and structures such as the larynx and nasopharynx.

A still further object of the present invention is to provide an optical viewing device for examining readily inaccessible body cavities that is capable of illuminating both the region to be examined and the region in which the instrument is positioned within the cavity.

Another object of the present invention is to reduce the amount of time required to accomplish visual examination of generally inaccessible body cavities and structure.

These and other objects of the present invention are attained by means of a laryngoscope of the like having a light reflecting mirror of a size and shape capable of being inserted into a relatively inaccessible body cavity, an elongated mirror support member being connected to the mirror for inserting and selectively positioning the mirror within the cavity to allow examination of the cavity, light transmitting means for directing a relatively small beam of light from a source of illumination positioned exterior the subject onto the surface of the mirror, the incident beam being located within a specific region offset from the central axis of the mirror, the axis of the light beam being angularly displaced in reference to the plane of the mirror to redirect the incident light back towards the central axis of the mirror, and a clear aperture formed in the mirror adjacent to the incident light beam whereby a portion of the illumination passes through the aperture and illuminates the region directly behind the mirror thereby facilitating positioning of the mirror within the cavity.

BRIEF DESCRIPTION OF THE DRAWINGS

For a better understanding of the invention as well as other objects and further features thereof, reference is had to the following detailed description of the invention to be read in conjunction with the accompanying drawings, wherein:

FIG. 1 is a side elevational view of a laryngoscope embodying the teachings of the present invention for carrying out an indirect examination of the larynx and like regions;

FIG. 2 is a partial view showing the mirror utilized in the device of FIG. 1 and further illustrating a light pipe arranged to direct a beam of light onto the mirror surface;

FIG. 3 is an enlarged view in partial section showing a source of illumination positioned adjacent to the light entrance face of the light pipe; and FIG. 4 is a side view in section showing the configuration of the mirror employed in the laryngoscope of FIG. 1.

DESCRIPTION OF THE PREFERRED EMBODIMENT

Referring initially to FIG. 1 there is shown a laryngoscope 10 designed to facilitate an examination of the larynx, nasopharynx and the like which embodies the teachings of the present invention. The assembly includes a power source 11, an illuminator subassembly 12, an elongated mirror support member 13, and a mirror 14. The power source can consist of a battery handle specifically adapted to be held in the hand of the examiner and (although not shown) typically includes a battery, switch and a rheostat control. As will become apparent from the description below, the battery handle provides a convenient means by which the examiner can position the mirror within a body cavity being examined and also provides power to a lamp for illuminating the cavity region.

As best seen in FIG. 3, illuminator subassembly 12 is arranged to be both electrically and mechanically connected to the battery handle by means of any suitable means, such as a quick connector adaptor or the like. Contained within the illuminator is a relatively high intensity lamp 17 that is arranged to direct illumination at the light entrance face 19 of light pipe 20. Preferably, the light source is a tungsten halogen lamp specifically adapted to operate efficiently with a light pipe.

Preferably, the light pipe is formed of a plurality of light transmitting optical glass fibers that are aligned into a bundle 22. The bundle is contained within a metal cylinder 24 that extends outwardly from the illuminator subassembly. As illustrated in FIG. 1, the cylinder takes an initial bend 27 upon leaving the illuminator subassembly and then makes a relatively straight run to its terminal end 28. The light exit face of the fiber optic bundle is located at about the terminal end of the cylinder with the plane of the light exit face being normal to the axial center line 29 of the cylinder. The axial center line of the cylinder also represents the center line of the fiber bundle. Both the light entrance face and the light exit face of the bundle are polished to provide for efficient transmission of the light therethrough. As can be seen, in this embodiment the heat of the lamp is confined to the proximal end of the bundle.

Mirror support member 13 basically consists of a straight elongated tubular element 30 which is passed over the light pipe in close sliding relationship therewith. A threaded coupling 36 is provided to secure tubular element 30 to the outer cylinder of the light pipe. Mirror 14 is mounted within a frame 40 having an extended arm 41 that is brazed or otherwise joined to the tubular element 30. By this arrangement, the mirror is securely positioned a predetermined distance from the exit face of the fiber bundle. The frame of the mirror is angularly offset in reference to the axial center line of the light pipe at an angle of about 40° to facilitate examination of the larynx and like regions.

As best illustrated in FIG. 2, the beam of light emitted from the light pipe is directed into the lower left hand quadrant of the mirror along the axis 29 of the light pipe. The exit face of the light pipe is positioned at a predetermined distance from the mirror surface whereby the incident light 48 does not flood the entire mirror surface and thus disturb the examiner who normally views along the central axis of the mirror as depicted by the dotted lines 47,49. As shown, the central axis of the light pipe is angularly offset in regard to the central axis of the mirror so that the reflected light path 45 thereof intersects the central axis 49 of the mirror at a determinable point 57 in the viewing plane of the mirror to provide efficient lighting in this region. As can be seen, by varying the angle of incidence, the point of intersection can be changed to accommodate various viewing distances. It should also be noted at this point, that the size and shape of the mirror is not critical and different type mirrors may be similarly employed in other applications.

As pointed out previously, one of the main problems encountered in utilizing a laryngeal mirror or the like is proper positioning of the mirror within a small generally inaccessible body cavity. As the mirror is introduced into the laryngeal cavity, the examiner must avoid contact with the sensitive areas and thus initiating a gag reflex in the subject. As the mirror moves into the cavity, the structure of the mirror itself serves to shadow the positioning region from most conventional light sources such as headlamps or the like. In other words, the examiner simply cannot see into the positioning region and must more or less intuitively feel for the proper position.

In the present invention, a small clear aperture 50 is formed in the reflecting surface of the mirror within the quadrant of the mirror containing the incident light. Some of the incident light is thus allowed to pass through the mirror to illuminate the region behind the mirror. The size, as well as the location, of the aperture in regard to the incident light is controlled to regulate the amount of light energy that is permitted to pass behind the mirror. In practice, a relatively small amount of light is required to sufficiently illuminate this region so that rapid and accurate positioning of the mirror can be accomplished.

Referring now more specifically to FIG. 4, it is preferred that the mirror have a spherical convex form as shown with the reflecting surface being the front surface 51 of the mirror. The vertex 53 of the mirror is preferably located upon the central axis thereof. By this arrangement, a relatively clear well defined, although slightly compressed, presentation within the viewing plane of the mirror is provided to the examiner with a minimum loss of illumination. The compressed view of the spherical convex mirror provides a larger field of view than a plano mirror, thus providing an easier and quicker means of locating the desired view with less chance of touching the sensitive areas of the cavity initiating a gag reflex or otherwise causing discomfort to the subject.

While this invention has been described with reference to the structure disclosed herein, it is not confined to the details set forth and this application is intended to cover any modifications or changes as may come within the scope of the following claims.

I claim:

1. A laryngoscope or the like for examining a generally inaccessible cavity of a subject having a mirror supported upon an elongated member for insertion and positioning within the cavity, the improvement comprising
   a light pipe arranged to bring illumination from a source exterior the subject and direct a beam of light upon a portion of said mirror; and
   an aperture passing through the reflecting surface of the mirror and being arranged to pass some of the light incident upon the mirror to illuminate the region behind said mirror.

2. The device of claim 1 wherein the center of the aperture is offset from the central axis of the light beam directed at said mirror to regulate the amount of light passing through the aperture.

3. The device of claim 2 wherein the central axis of the light beam is angularly offset in reference with the plane of the mirror whereby the incident light is reflected back toward the central axis of the mirror.

4. Apparatus such as a laryngoscope and the like for examining relatively inaccessible cavities of a subject including
   a mirror secured to an elongated support element for inserting and selectively positioning the mirror within the cavity;
   a light pipe generally aligned with said elongated support element and being arranged to focus a beam of light from a source positioned exterior the subject onto a specific area of the mirror, said area being removed from the central axis of said mirror;
   an aperture in said mirror for passing at least a portion of the incident light through said mirror to illuminate the region behind said mirror; and
   the axis of the directed light beam being angularly displaced in reference to the plane of the mirror whereby the incident light is reflected back toward the central axis of the mirror in the viewing plane.

5. The apparatus of claim 4 wherein said support element includes a tubular element through which the light pipe is passed in close sliding relationship therewith.

6. The apparatus of claim 4 wherein the light pipe includes a fiber optic bundle having a light entrance face positioned adjacent a source of illumination and a light exit face positioned a predetermined distance from the mirror.

7. The apparatus of claim 4 wherein the center of the aperture is offset from the axis of the light beam incident upon the mirror a predetermined distance to regulate the amount of light passing through said aperture.

8. The apparatus of claim 7 wherein the mirror is a spherical convex mirror having its vertex lying upon the central axis of the mirror.

9. The apparatus of claim 8 wherein the mirror is generally rectangular in shape with the incident light beam being generally aligned along one of the diagonals of said rectangle.

10. The apparatus of claim 8 wherein the mirror is generally circular in shape.

11. The apparatus of claim 4 wherein the light source comprises a high intensity lamp positioned adjacent to the light entrance face of the fiber optics bundle and a battery electrically connected to said lamp.

12. The apparatus of claim 4 wherein the central axis of the mirror is angularly displaced in reference to the axis of the elongated support element to facilitate examination of relatively inaccessible regions within the cavity.

* * * * *